United States Patent [19]

Bard et al.

[11] 4,303,486

[45] Dec. 1, 1981

[54] METHODS OF PHOTOCATALYTIC DECARBOXYLATION OF SATURATED CARBOXYLIC ACID

[75] Inventors: Allen J. Bard, Austin, Tex.; Bernhard Kraeutler, Zurich, Switzerland

[73] Assignee: Board of Regents, University of Texas System, Austin, Tex.

[21] Appl. No.: 24,520

[22] Filed: Mar. 28, 1979

[51] Int. Cl.³ ............................................. C07C 3/24
[52] U.S. Cl. ............................................. 204/162 R
[58] Field of Search ................................... 204/162 R

[56] References Cited

U.S. PATENT DOCUMENTS 2,940,913  6/1960  McKusick ........................ 204/154
2,940,914  6/1960  Hoover ............................ 204/154

OTHER PUBLICATIONS

Frank et al., J. Am. Chem. Soc., vol. 99, pp. 303 and 304 (1977).
Frank et al., Journal of Physical Chemistry, vol. 81, No. 15, pp. 1484–1488 (1977).
Kraeutler et al. (1), J. Am. Chem. Soc., vol. 99, pp. 7729–7731 (1977).
Kraeutler et al. (2), J. Am. Chem. Soc., vol. 100, pp. 4903–4905, (Jul. 5, 1978).

Primary Examiner—Brooks H. Hunt
Attorney, Agent, or Firm—Arnold, White & Durkee

[57] ABSTRACT

Methods for heterogeneous photocatalytic decarboxylation of saturated carboxylic acids on several n-type semiconductor powders are disclosed. Major reaction products are the corresponding alkanes and carbon dioxide.

22 Claims, No Drawings

METHODS OF PHOTOCATALYTIC DECARBOXYLATION OF SATURATED CARBOXYLIC ACID

BACKGROUND OF THE INVENTION

This invention relates to decarboxylation of saturated carboxylic acids on semiconductor powders.

Applicants discussed background information relative to their invention in a paper published at 100 *Journal of the American Chemical Society* 5985 (1978) which paper is hereinafter referred to as "applicants' paper". In applicants' paper, different types of photoelectrochemical processes were discussed, and it was noted that semiconductor materials are of central importance in electrochemical systems which can utilize solar energy for the production of electricity or new chemical species.

In photoelectrochemical cells operating in the *photovoltaic* mode, the light which irradiates the semiconductor-solution interface is converted into electricity ideally with no change in the composition of the solution or the semiconductor material (See FIG. 1a in applicants' paper). The driving force in such a cell is the underpotential developed for an oxidation at the n-type photoanode (or a reduction at a p-type photocathode).

In *photoelectrosynthesis* the light is used to drive an overall cell reaction in a nonspontaneous direction so that the radiant energy is stored as chemical energy (e.g., in fuels) (See FIG. 1b in applicants' paper). Although earlier studies in this area were concerned with the photolysis of water (i.e., production of $H_2$ and $O_2$), studies of photooxidations of other solution species at n-type semiconductor electrodes have subsequently provided information about the mechanism of such photoassisted processes, and have been extended to the bulk synthesis of other chemical species.

In *photocatalysis* a reaction is driven in a spontaneous direction by the light; radiant energy overcomes the energy of activation of the process (See FIG. 1c in applicants' paper). Cells which operate simultaneously in the photovoltaic and photoelectrosynthetic or photocatalytic modes are also possible.

While photoredox processes in homogeneous solutions are usually inefficient, the electric field (or band bending) at the photoexcited semiconductor-solution interface causes rapid separation of the carriers and thus inhibits recombination of the highly reactive light-generated electron-hole pair. Furthermore, the primary product of electron transfer at the semiconductor-solution interface often does not suffer rapid back-donation of the electron from the electrode, as overpotentials for redox processes involving energy levels in the forbidden band gaps of the semiconductor may be considerable. Thus high quantum yields can be obtained in heterogeneous photoredox processes. Moreover, fast, irreversible chemical reactions of the solution species following the electron transfer can compete with the reverse charge transfer at the electrode. With this in mind and to extend the scope of synthetic methods at illuminated semiconductors, applicants had earlier investigated a chemical electrosynthetic reaction, the Kolbe decarboxylation of carboxylic acids.

The well known Kolbe synthesis may be illustrated in the case of ethane from sodium acetate as follows:

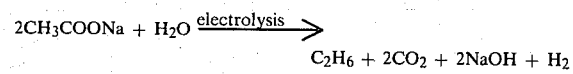

where the first two reaction products illustrated above are formed at the anode and the latter two at the cathode.

The Kolbe reaction does not appear to be an attractive one in the search for an energy-storing system, since the cleavage product, carbon dioxide, renders most simple decarboxylations exoenergetic. Moreover, a high oxidation potential is needed for initiation of the Kolbe reaction on metal electrodes and many semiconductors (e.g., ZnO, CdS) show limited stability against photodecomposition under strongly oxidizing conditions. Therefore, among the variety of investigated photoinduced oxidation processes at n-type semiconductor materials the Kolbe reaction has previously received only minor attention.

In earlier studies of the applicants, reported in 1977 at 99 *Journal of the American Chemical Society* 7729 (1977) applicants reported on the photoassisted oxidation of acetate ion to ethane in a acetonitrile solution at n-type titanium dioxide electrodes in both the single crystal and chemically vapor deposited polycrystalline form. In that earlier paper, applicants reported a reaction mechanism that follows that for other photoassisted oxidations at n-$TiO_2$. There, they had reported that light of energy greater than $E_g$ causes formation of electron-hole pairs. When the potential of the semiconductor is positive of the flat-band potential, the bands are bent upward and the photogenerated holes (p+) migrate to the electrode surface while the electrons drift to the bulk of the electrode, thus preventing recombination. The holes, at energies characteristic of the valence band or low-lying surface states, are effectively strong oxidizing agents and can abstract electrons from acetate ions initiating the cascade of steps in the Kolbe reaction:

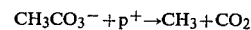

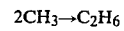

Since the photo-Kolbe reaction occurs at potentials of approximately 2.4 V more negatively than those for the oxidation at platinum, the effective efficiency of utilization of the excitation energy is high. The chemical irreversibility of the overall process prevents back-donation of electrons from the electrode and leads to an overall high efficiency for the process. The potential for the photo-oxidation of acetate is negative of that for the onset of hydrogen ion reduction in the acetate/acetic acid mixture, suggesting that photoelectrolysis with little or no external applied voltage leading to a mixture of ethane and hydrogen is possible. Furthermore, the control of current density via the light flux and the possible suppression of undesirable 2-electron oxidations by use of photoinduced electron transfer at a wide band gap semiconductor (e.g., $TiO_2$) are also of interest with respect to the Kolbe electrosynthesis.

SUMMARY OF THE INVENTION

This invention relates to the decarboxylation of a saturated carboxylic acid by irradiating a suspension of the proper catalysts in a solution containing the acid.

The invention contemplates the suspension of an appropriate catalyst, for example an n-type $TiO_2$ powder, in an aqueous solution containing a carboxylic acid. The suspension is irradiated and decarboxylation occurs resulting in the formation of the corresponding alkane to the carboxylic acid and carbon dioxide as the primary reaction products. The reaction occurs at ambient temperature.

Embodiments of the invention are discussed wherein various types of saturated carboxylic acids are employed. Also, embodiments are discussed both in the presence of oxygen and in the absence of oxygen.

DETAILED DESCRIPTION OF PREFERRED EMBODIMENTS

The following discussion is in terms of the preferred embodiments of this invention, which represent the best mode known to the inventors at the time of this application.

In accordance with the preferred embodiments of this invention, a suitable catalyst is provided in the form of an n-type semiconductor powder. One suitable catalyst for use in this reaction is n-type $TiO_2$ powder. The particular type of powder used may desirably be metalized. In many contexts of use, the powder may preferably be anatase doped, platinized, but other suitable powders such as anatase undoped, platinized or anatase, doped or anatase, undoped may be employed. A partially platinized powder is particularly preferred.

Further in accordance with such embodiments, the catalyst is mixed in a solution containing a saturated carboxylic acid. A suitable carboxylic acid is, for example, acetic acid or pivalic acid. Mixtures of saturated carboxylic acid, or mixtures of carboxylic acids and acetates (e.g., NaAc) may also be utilized.

Further in accordance with the preferred embodiments of the invention, the carboxylic acid is mixed in aqueous solution, to which the semiconductor powder (e.g., 100 mg in 15 mL solution) is added as a catalyst.

The solution is then irradiated desirably at ambient temperature with, for example, a xenon lamp. The irradiation will cause the temperature of the solution to rise to some higher temperature, often around 55° C., which was the temperature measured in many of the experimental results of applicants.

The solution is irradiated for at least a time sufficient for the evolution of carbon dioxide. If the solution is not already saturated with $CO_2$, then the first carbon dioxide evolved will be dissolved in the solution and will not be visible. The actual time of irradiation may desirably be much longer than the minimum time indicated above. For example, if a method of the invention is utilized for chemical synthesis, it may be desirable to continue the irradiation for several hours. On the other hand, if the method is being used to remove pollutants, and the differential between actual concentration [of e.g., acetate] and the required concentration is small, then a very short period of irradiation may be sufficient.

Reaction products are formed which comprise the alkane corresponding to the carboxylic acid, and carbon dioxide.

The preferred embodiments of this invention are better illustrated by the examples which follow. In Examples 6–58, the following materials were employed:

Acetic acid (HAc, glacial, Fisher Scientific Co.), monodeuterioacetic acid (DAc, 98% D, Aldrich Chemical Co.), deuterated water ($D_2O$, 99.7% $d_2$, Merck Sharp & Dohme), propionic acid (Baker grade, Baker Chemical Co.), n-butyric acid (reagent grade, Matheson Coleman and Bell), n-valeric acid (99+%, Aldrich Chemical Co.), pivalic acid (99+%, Aldrich Chemical Co.), adamantane-1-carboxylic acid (99%, Aldrich Chemical Co.), tetra-n-butylammonium hydroxide (titration grade, 1.0 M in $H_2O$, Southwestern Analytical Chemical Inc.), acetonitrile (ACN, spectrograde, Matheson Coleman and Bell), n-pentane (spectograde, Matheson Coleman and Bell) and n-heptane (American Drug & Chemical) were used without further purification.

The $TiO_2$ powders were anatase, undoped (reagent, Matheson Coleman and Bell), confirmed by X-ray to be 99% pure anatase, particle size 125–250 $\mu m$ and grain size 0.2 $\mu m$, geometric surface area 1–10 $m^2/g$); doped anatase (produced from the undoped anatase by heating under a hydrogen atmosphere at 650° C. for 8 h; by X-ray $\sim$10% rutile, $\sim$90% anatase); undoped rutile (produced by heating the undoped anatase under air at 1100° C. for 26 h; by X-ray >99% rutile); doped rutile (produced by heating undoped rutile under $H_2$ for 12 h at 850° C.). The powders were platinized by photodecomposition of hexochloroplatinate solutions and contained $\sim$1–5% platinum by weight.

The apparatus used included a 2500-W Xe-Hg lamp (Model UF 30 KK, Christie Electric Corp., Los Angeles, Calif.), operated at 1600 W (hereafter simply called the 2500-W Xe-Hg lamp). This lamp was used as the light source for most preparative runs; a 450-W Xe lamp with Model 6242 power supply (Oriel Corp., Stamford, Conn.) served in several analytical runs. The reaction cell and the water bath were both of Pyrex; the bath temperature usually was set to 55°±3° C.

Irradiation was performed by illuminating the sample (a stirred suspension of typically 100 mg of powder in 15–20 mL of solution) through the water bath and a flat window on the Pyrex cell. Gas chromatography of reaction gases was done on a Porapak Q column with an Aerograph Hy-Fi Model 600 C instrument. Mass spectral analyses were routinely done on a Model 21-491 Du Pont mass spectrometer. H NMR spectra were taken on a Varian A-60B and C NMR spectra were obtained with a Bruker WH-90 instrument.

The gases produced during the irradiations under inert atmosphere were collected in a mercury-containing gas volumetric apparatus. The increase of gas volume, as determined at 1 atm and at constant temperature, was taken as the total volume of the gases evolved upon illumination. After termination of each photolysis, a directly attached, evacuated gas sample cell for use in analysis by mass spectrometry was filled with the gas mixture in the volumetric apparatus. At the same time a sample was taken for gas chromatographic analysis (GC). The reaction cell then was uncoupled from the gas volumetric system and purged with nitrogen for about half an hour.

The rate of carbon dioxide evolution was determined gravimetrically in a subsequent run. The reaction gases were swept out of the reaction vessel with a stream of nitrogen and were bubbled through a saturated solution of $Ba(OH)_2$ in 1 M NaOH. The precipitated $BaCO_3$ was filtered off, washed well with distilled water, dried at 120° C., and weighed.

The analytical data for the evolved gas are discussed in applicants' paper.

EXAMPLE 1

For a control experiment, a deaerated suspension of 100 mg of untreated $TiO_2$ powder in a mixture of 4.5 mL of glacial acetic acid and 45 mL of distilled water was prepared, and the suspension was retained in a Pyrex cell. At a temperature of 55° C. the suspension was irradiated with white light from a 2500-W xenon lamp (operated at 1600 W).

Measurements showed that only minute amounts of $CO_2$ (trapped as $BaCO_3$) were produced, corresponding to about 2 μmol/h.

EXAMPLE 2

As a further control experiment, Example 1 was repeated except that $TiO_2$ powder was not added to the suspension.

Results similar to those of Example 1 were observed.

EXAMPLE 3

A deaerated suspension of 100 mg of platinized n-type $TiO_2$ (anatase) powder in a mixture of 4.5 mL of glacial acetic acid and 45 mL of distilled water was prepared, and the suspension was retained in a Pyrex cell. At a temperature of 55° C. the suspension was illuminated with white light from a 2500-W xenon lamp (operated at 1600 W).

A continuous stream of gas bubbles was observed to rise out of the depth of the solution near the illuminated area. These gaseous products, which accumulated at a rate of 8.1 mL/h were collected in a gas volumetric system and analyzed by mass spectroscopy and gas chromatography. The mass spectrum [m/e (rel intensity)] consisted of signals of carbon dioxide, 44(100); ethane, 30(2), 29(1.5), 28($\sim$7), 27(2), 26(1.5); methane, 16(91), 15(79), 14(5); and hydrogen, 2(4), with small background signals due to air [oxygen, 32(2); nitrogen, 28($\sim$8)]; and water, 18(13). The ratio of methane to ethane of the gaseous products was estimated by gas chromatography to be 11:1.

EXAMPLE 4

Example 3 was repeated with the same reactants in the same amounts and under identical conditions. In this experiment, the yield of $CO_2$ was determined quantitatively to account for 160 μmol/h (corresponding to 3.7 mL of gas at 1 atm) and therefore for about half the volume of the gaseous reaction products, in full accord with the reaction:

$$CH_3CO_2H \rightarrow CH_4 + CO_2.$$

The dominant reaction products of the decomposition of acetic acid were carbon dioxide and methane (ratio $\sim$1:1); only small amounts of ethane and hydrogen were formed (total $\sim$10 vol %, in roughly a ratio of 1:1).

EXAMPLE 5

Example 3 was repeated, except that the acetic acid used contained 0.8 M sodium acetate.

From this experiment, it was determined that quantitatively and qualitatively similar results to those obtained in Examples 3 and 4 were obtained.

From Examples 3, 4, and 5, side reactions attributable to photocatalytic decomposition of water appeared to be unimportant.

EXAMPLES 6–14

In the next group of experiments, the photocatalytic decomposition of aqueous mixtures of acetic acid and sodium acetate on undoped anatase powders in the presence of oxygen was studied.

Suspensions of 200 mg of undoped anatase powders in 15 mL of aqueous solutions of acetic acid/sodium acetate were prepared. The temperature of the suspensions was kept at 55° C., except for that of Example 7 which was kept at 42° C.

In the presence of 1 atm oxygen, the suspensions were irradiated with the full output of a 2500-W xenon lamp; oxygen was passed through the reaction mixture continuously and was used to carry the volatile reaction products into a saturated solution of $Ba(OH)_2$ in 1 M NaOH, causing the $CO_2$ to be precipitated as $BaCO_3$. This was weighed and the $CO_2$ evolution rate determined.

Results were as follows:

| Example | total concn of acetate, M | pH | illumination time, h | $BaCO_3$ yield, mg | rate of evol. of $CO_2$ μmol/h |
|---|---|---|---|---|---|
| 6 | 5 | 3.4 | 5 | 185 | 190 |
| 7 | 5 | 3.4 | 3 | 62 | 111 |
| 8 | 0.5 | 3.4 | 3.75 | 81 | 110 |
| 9 | 0.05 | 3.4 | 3.5 | 64 | 94 |
| 10 | 0.02 | 3.4 | 2.5 | 42 | 86 |
| 11 | 5 | 4.7 | 5 | 61 | 62 |
| 12 | 0.5 | 4.7 | 3.2 | 76 | 122 |
| 13 | 0.05 | 4.7 | 3.2 | 77 | 123 |
| 14 | 0.02 | 4.7 | 1.5 | 26 | 87 |

It is noted that lowering the temperature from 55° C. to 42° C. resulted in a noticeable decrease in evolution of carbon dioxide. It is also noted that decreasing the acetate concentration from 0.5 to 0.02 at a pH of 3.4 only decreased the evolution of carbon dioxide by a factor of about 2. At a pH of 4.7, high acetate concentrations actually appear to inhibit the evolution of carbon dioxide.

EXAMPLES 15–23

Another series of tests (designated Examples 15–20) similar to those of Examples 6–14 was performed, except that the catalyst material was changed to determine the effect of the catalyst material on the rate of photocatalytic evolution of carbon dioxide in the presence of oxygen. All of these tests were performed at 55° C. except Example 17, which was performed at 65° C. The results of these tests and further control experiments designated Examples 21–23 are indicated below:

| Example | catalyst | solution composition, total conc. | time, h | yield (mg BaCO3) | Rate of CO2 evol in μmol/h |
|---|---|---|---|---|---|
| 15 | none | 5 M NaAc/HAc (1:20) | 4 | 2 | 2.5 |
| 16 | TiO2 (anatase, undoped) | 5 M NaAc/HAc (1:20) | 5 | 185 | 190 |
| 17 | TiO2 (anatase, doped) | 0.5 M NaAc/HAc (1:1) | 3 | 110 | 185 |
| 18 | TiO2 (rutile, doped) | 5 M NaAc/HAc (1:20) | 2 | 27 | 68 |
| 19 | TiO2 (anatase, undoped, platinized) | 0.8 M HAc | 2 | 171 | 440 |
| 20 | TiO2 (rutile, doped, platinized) | 0.8 M HAc | 3.5 | 70 | 105 |
| Control Experiments | | | | | |
| 21 | TiO2 (anatase, undoped) | 5 M NaAc/HAc (1:20) | 12/dark | 0 | 0 |
| 22 | TiO2 (anatase, undoped) | 5 M NaAc/HAc (1:1) | 4* | 27 | 34 |
| 23 | TiO2 (anatase, undoped) | 1 M NaAc/HAc (1:10) +0.2M H2O2 | 15/dark | 25 | 8.8 |

*In Example 22, the light source was the full output of a 450-W Xe lamp.

It is observed from the above results that anatase proved to be somewhat more active than rutile, with little influence of doping, but a significant reactivity increase resulted from partial platinization of the powders.

EXAMPLES 24–32

A further group of experiments, designated Examples 24–32, was performed to measure the activity of a variety of n-type $TiO_2$ powders for the photocatalytic decomposition of oxygen-free acetic acid.

In these experiments, 100 mg of $TiO_2$ powder was stirred in a suspension of 1 g. NaAc in 15 mL of acetic acid (except for Example 26, where HAc 10 vol.% in $H_2O$ was used, and Example 30, where pure acetic acid was used). The full output of a 2500-W Xe-Hg lamp (except for Example 27, where the lamp was a 2500-W Xe lamp and Example 32, where a 450-W Xe lamp was employed) operated at 1600 W was focused on an area of approximately 5 square centimeters on the flat Pyrex window of the reaction vessel, at 55°±3° C. (except for Example 31, which was performed at 45° C.).

Even with this high light intensity, the amount of suspended powder completely absorbed the light in the front half of the cell. The activity of the powders for the photocatalytic decomposition of acetic acid was again estimated from the yield of carbon dioxide, determined gravimetrically as $BaCO_3$.

The results are shown below as Examples 24–32:

| Example | Catalyst | time/h | yield of BaCO3, mg | rate of evol of CO2, μmol/h | rel ra |
|---|---|---|---|---|---|
| 24 | rutile, undoped | 5 | 3 | 2 | 0.15 |
| 25 | rutile, doped | 5 | 2 | 2 | 0.15 |
| 26 | rutile, doped platinized | 3 | 2.5 | 4 | 0.31 |
| 27 | anatase, undoped | 6 | 15 | 13 | 1 |
| 28 | anatase, doped | 5 | 58 | 59 | 4.5 |
| 29 | anatase, undoped, platinized | 4.75 | 140 | 150 | 11.5 |
| 30 | anatase, doped, platinized | 1.1 | 75 | 360 | 28 |
| 31 | anatase, doped, platinized | 2.7 | 121 | 230 | 17.5 |
| 32 | anatase, doped, platinized | 3.7 | 18 | 25 | 1.9 |

As is seen from the above results, all the rutile powders lead to only little evolution of carbon dioxide. On the other hand, anatase powders were quite reactive photocatalysts in the order undoped < doped < undoped, platinized < doped, platinized.

EXAMPLES 33–36

In a further series of experiments, the effect of water on the photocatalytic decomposition of oxygen-free acetic acid on undoped, platinized anatase powders were investigated.

Suspensions of 100 mg of catalyst powder in 15 mL of glacial acetic acid at 55° C. under nitrogen were irradiated with a 2500-W Xe-Hg lamp at 1600 W. The rate of carbon dioxide evolution is shown below for various concentrations of water:

| Example | vol % water | illumination time, h | yield of $BaCO_3$, in mg | rate of evol of $CO_2$ in mol/h |
|---|---|---|---|---|
| 33 | 0 | 5.5 | 175 | 160 |
| 34 | 5 | 3.25 | 110 | 170 |
| 35 | 50 | 3.7 | 108 | 153 |
| 36 | 95 | 3 | 71 | 123 |

It is seen that, except for very dilute solutions, dilution of the acetic acid with water did not seriously affect the results.

EXAMPLES 37–42

Other experiments were performed to analyze the gaseous reaction products of the decarboxylation reactions of the type reported in the preceding experiments, and the results of these analyses are reported as Examples 37–42.

These reaction products were formed by irradiating with a 2500-W Xe-Hg lamp operated at 1600 W, under nitrogen, at 55° C., 100 mg $TiO_2$ powder in 15–20 mL solution. Different catalysts were employed as indicated in the summary which follows:

| Example | Catalyst | solution composition | total gas rate | $CO_2$ $\mu$mol/h | methane: ethane | $D_2$:HD:$H_2$ |
|---|---|---|---|---|---|---|
| 37 | anatase, undoped, platinized | HAc | 4.2 | | 19:1 | 0:0:1 |
| 38 | anatase, undoped, platinized | HAc 10 vol % in $H_2O$ | 8.1 | 3.5 | 11:1 | 0:0:1 |
| 39 | anatase, doped, platinized | HAc | 15.5 | 8.1 | 8:1 | 0:0:1 |
| 40 | anatase, undoped, platinized | HAc 10 vol % in $D_2O$ | 5.6 | | 15:1 | |
| 41 | anatase, doped, platinized | DAc (98% D) | 8.1 | | 15:1 | 2:0.6:1 |
| 42 | anatase, doped, platinized | DAc (95% D) | 8.0 | 5.1 | 20:1 | 2:1.1:0.6 |

The major hydrocarbon product was methane, along with $CO_2$, per the reaction $$CH_3CO_2H \rightarrow CH_4 + CO_2$$

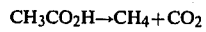

plus only small amounts of hydrogen gas and ethane per the reaction $$2CH_3CO_2H \rightarrow CH_3CH_3 + 2CO_2 + H_2$$

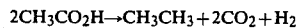

Ethane, the usual Kolbe product from acetic acid/acetate electrolysis, was formed in only 5–10% yield, with a tendency to an increased fraction of ethane with increasing rate of gas evolution, as clearly established by mass spectrometry and gas chromatography. In the absence of molecular oxygen, side reactions leading to nonvolatile hydrocarbon derivatives (e.g., $CH_3OH$) were insignificant, as shown by comparison of the rates of $CO_2$ evolution and total gas production.

In accord with the equations shown above, carbon dioxide amounted to about half of the total gas volume, even for the photodecomposition of acetic acid from reaction mixtures containing only 10 vol% acetic acid in water.

EXAMPLE 43

In another experiment, it was determined that solar irradiation also readily photocatalyzed the decomposition of oxygen-free acetic acid on platinized anatase. An air-tight culture flask was filled with 4 L of glacial acetic acid containing 1 g of sodium acetate and its flat bottom (diameter 20 cm. area 314 cm$^2$) was covered with a thin layer of 400 mg of platinized, doped anatase powder (containing ~1% Pt). This reaction mixture was flushed with nitrogen for 16 h at room temperature to remove oxygen. Then the flask was exposed to sunlight for 12 days, partly cloudy skies and high temperature of 25° C.

A weak stream of nitrogen, constantly purging the reaction mixture, served to keep out $O_2$ and carried the $CO_2$ and the other volatile reaction products out of the flask and through a solution of $Ba(OH)_2$ in 1 M NaOH where a precipitate of $BaCO_3$ was formed. The amount of $BaCO_3$ formed was determined regularly and gave a total of 978 mg of $BaCO_3$ (4.98 mmol).

In the absence of oxygen, the rate of decomposition of acetic acid could thus be estimated to be 415 $\mu$mol/day or 1.3 $\mu$mol/day-cm$^2$. A mass spectral and gas chromatographic analysis of the reaction products showed $CO_2$ and methane; ethane was not found. Moreover, comparison of the weight of the powder before (380 mg) and after the experiment (368 mg) showed good stability of the photocatalyst under the conditions, allowing for the loss of powder on recovery from the large volume of solution.

EXAMPLE 44

A mixture of 100 mg of doped, platinized anatase powder was stirred into 600 $\mu$L of acetic acid, 80 mg of sodium acetate, and 20 mL of ACN. The solution was irradiated at 55° C. with a 2500-W Xe-Hg lamp to yield methane, carbon dioxide, hydrogen and ethane at a total rate of 7.9 mL/h, corresponding to a rate of decarboxylation of about 170 $\mu$mol/h.

EXAMPLES 45-58

Further experiments were performed to ascertain whether the decarboxylation reaction as described above would be applicable to other saturated carboxylic acids of higher molecular weight. In the first group of these experiments, designated Examples 45-51, the photocatalytic decarboxylation of acetic acid was explored in three aprotic solvents, acetonitrile, methylchloride, and hexane.

One hundred mg of $TiO_2$ photocatalyst was mixed in 15 to 20 mL of solution at 55° C. under nitrogen, and irradiated with a 2500-W Xe-Hg lamp at 1600 W. The photocatalyst was a doped, platinized anatase powder, and in these experiments oxygen-free acetic acid was mixed with a cosolvent as indicated in the various examples. In Example 48, 80 mg of sodium acetate was mixed in 20 mL of solution. The results of these experiments are shown below:

| Example | cosolvent | salt | temp, °C. | rate of $CO_2$ evolution, mol/h |
|---|---|---|---|---|
| 45 | none | | 55 | 360 |
| 46 | $H_2O$ (90 vol %) | | 55 | 406 |
| 47 | ACN (97 vol %) | | 36 | 95 |
| 48 | ACN (97 vol %) | NaAc | 36 | 130 |
| 49 | $CH_2Cl_2$ (90 vol %) | | 30 | 128 |
| 50 | $C_6H_6$ (90 vol%) | | 39 | 50 |
| 51 | $C_6H_6$ (90 vol %) | | 55 | 77 |

It is seen that the rate of carbon dioxide evolution was lower for the aprotic solvents, but it was determined that the decomposition products of acetic acid in acetonitrile were still mainly methane and carbon dioxide, together with approximately 10% hydrogen and ethane.

In Examples 52-58, other saturated carboxylic acids were investigated as listed in the results tabulated below. In these experiments, 100 mg of platinized, doped anatase powders [except in Example 53 where undoped, platinized anatase was employed] was stirred in 20 mL solution at 56°±3° C., under nitrogen. The solution was illuminated with a 2500-W Xe-Hg lamp at a power level of 1600 W.

tion occurred only for the decarboxylation products of pivalic acid (tetrabutyl radical, R=Me), and the possibility of propionic acid (ethyl radical, R=H),

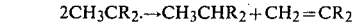

as shown in the mass spectrum of the reaction gases. In aqueous solutions the rates of decarboxylation were similar for the acids investigated. Adamantane-1-carboxylic acid, dissolved in ACN at a much lower concentration (~0.12 M), was found to decarboxylate at a significantly lower rate than the other acids with a decrease in rate as the photolysis proceeded (initial rate, 65 μmol/h; final rate, after 62% conversion, 28 μmol/h). However, the corresponding alkane, adamantane, was again formed in 58% yield by decarboxylation of this bridgehead carboxylic acid. A noise decoupled C NMR spectrum showed only two nonequivalent carbon atoms, yielding definite proof of the product, owing to its high symmetry. The usual electrochemical Kolbe reaction for these acids produces predominantly dimer with smaller amounts of the alkene. For the adamantane-1-carboxylic acid the Kolbe reaction, carried out in an alcoholic medium at a metal electrode, produces 1-alkoxyadamantane.

Further experiments have been performed using instead of $TiO_2$ powders, powders of other large bandgap semiconductors. Photodecomposition of carboxylic acids utilizing other such powders, such as $WO_3$, in the presence of oxygen, has also been found to result in the evolution of carbon dioxide.

BRIEF DISCUSSION OF EXPERIMENTAL RESULTS

From the experiments reported as Examples 1-58 above, it was determined that irradiating a suspension of n-type $TiO_2$ powders in a saturated carboxylic acid, which may include the salt of a carboxylic acid, at ambient temperature in the presence of absence of oxygen, results in decarboxylation to the corresponding alkane with approximately equal amounts of the alkane and carbon dioxide being formed.

From Examples 1-5, it was found that carbon dioxide accounted for approximately one-half the reaction products and that the ratio of methane:ethane was about

| Example | acid | solvent (ratio volume) | yield of gas; mL/h | major products | minor products |
|---|---|---|---|---|---|
| 52 | acetic acid | | 15.5 | $CH_4,CO_2$ | $CH_3CH_3,H_2$ |
| 53 | acetic acid | $H_2O(1:10)$ | 8.1 | $CH_4,CO_2$ | $CH_3CH_3,H_2$ |
| 54 | propionic acid | $H_2O(1:10)$ | 19 | $CH_3CH_3,CO_2$ | $CH_2=CH_2,H_2$ |
| 55 | n-butyric acid | $H_2O(1:12)$ | 9.4 | propane,$CO_2$ | $H_2$ |
| 56 | n-valeric acid | $H_2O(1:20)$ | 16 | n-butane, | $H_2$ |
| 57 | pivalic acid | ACN/$H_2O$ (1:10:10) | 6 | isobutane, $CO_2$ | isobutylene, $H_2$ |
| 58 | adamantane 1-carboxylic acid | * | 65/ μmol/h $CO_2$ | adamantane, $CO_2$ | |

*360 mg of adamantane-1-carboxylic acid (2 mmol) in 15 mL of ACN and 1.5 mL of n-heptane.

In all of these cases the decarboxylation to the corresponding alkane by the following reaction.

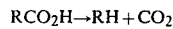

appeared to proceed cleanly, Kolbe dimers were found only for decarboxylation of acetic acid, as ethane. Side reactions due to disproportionation via H-atom abstrac- 11:1, when platinized anatase powders were added to acetic acid or acetic acid/sodium acetate mixtures.

From Examples 6-14, it was found that the evolution of carbon dioxide was relatively independent of the total concentration of acetate within at least certain limits, and that lowering the temperature of the solution from about 55° C. to about 42° C. did noticeably decrease the evolution of carbon dioxide.

Various catalyst materials were examined in Examples 15-23, and from these examples it was learned that anatase powders were more active than rutile, and that platinization of the powders promoted greater reactivity. Various mixtures of acetic acid and sodium acetate were tested, for periods ranging from two to five hours.

Similar experiments were conducted as Examples 24-32 in the absence of oxygen, and similar results were obtained.

Here it was concluded that rutile powders were relatively unreactive, but that anatase powders were reactive photocatalysts in increasing order of reactivity as follows: undoped; doped; undoped, platinized; doped, platinized.

From Examples 33-36 it was determined that the dilution of acetic acid with water had relatively little effect on the reaction until the solution was highly dilute.

In Examples 37-42, the reaction products were analyzed. From these examples, it was determined that the major reaction products from these reactions of acetic and monodeuterioacetic acids were carbon dioxide and methane, and the methane:ethane ratio ranged from 8:1 to 20:1.

Solar irradiation was found to photocatalyze the decomposition of acetic acid on platinized anatase in Example 43. From this experiment it was also determined that operable reactions occur at ambient temperature as well as the elevated temperatures caused by irradiation.

Similar reaction products were found from the reaction of acetic acid (or acetic acid and sodium acetate) in various aprotic solvents in Examples 44-51.

The decarboxylation of various other saturated carboxylic acids were studied in Examples 52-58, and it was observed that a similar reaction occurs.

The decarboxylation of all the carboxylic acids studied yielded the corresponding alkane as the main product. This is true even for tertiary and bridgehead carboxylic acids, which are difficult to decarboxylate thermally.

UTILITY

The methods described in this application are useful in small scale chemical synthesis. For example, such methods are useful in the pharmaceutical industry, since decarboxylation reactions are difficult.

Further, such methods are useful in the removal of pollutants such as acetate from waste streams, for the capture of solar energy, and for the production of methane.

The following claims more particularly define our invention. Obvious changes may be made in the methods claimed without departing from the scope of our invention.

We claim:

1. A method for decarboxylating an aliphatic carboxylic acid solution comprising:
   providing an aliphatic carboxylic acid solution;
   providing a suitable n-type semiconductor powder;
   mixing said powder in said carboxylic acid solution to form a mixture;
   irradiating said mixture at a temperature and for a time sufficient for the evolution of carbon dioxide gas;
   to form as the major reaction products carbon dioxide and the alkane corresponding to the carboxylic acid of said solution.

2. The method in accordance with claim 1, wherein said semiconductor powder is $TiO_2$.

3. The method in accordance with claim 2, wherein said $TiO_2$ powder is partially platinized.

4. The method in accordance with claim 2, wherein said $TiO_2$ powder is selected from the group consisting of anatase doped, anatase undoped, anatase doped platinized, and anatase undoped platinized.

5. The method of claim 1 wherein the mixture is irradiated at ambient temperature, causing the temperature of the solution to rise at at least about 52° C.

6. The method in accordance with claim 1 wherein said mixture is irradiated in the absence of oxygen.

7. The method in accordance with claim 1 wherein said carboxylic acid solution is an aqueous solution.

8. The method in accordance with claim 1 wherein said carboxylic acid solution comprises, in aqueous solution, a saturated carboxylic acid selected from the group consisting of acetic, propionic, n-butyric, n-valeric, pivalic and adamante-1-carboxylic, and combinations thereof.

9. The method in accordance with claim 1 wherein said carboxylic acid solution comprises, in aqueous solution, a saturated carboxylic acid and an acetate salt.

10. The method in accordance with claim 9 wherein said carboxylic acid is acetic acid and said salt is sodium acetate.

11. A method for the heterogeneous decarboxylation of an aliphatic carboxylic acid solution comprising:
    providing an aliphatic carboxylic acid solution;
    providing an n-type $TiO_2$ powder;
    mixing at least about 5 mg of said powder per mL in said solution to form a mixture;
    irradiating said mixture, causing the temperature of said mixture to rise to at least about 42° C., and continuing said irradiation for a time sufficient for the evolution of carbon dioxide gas;
    to form as the major reaction products carbon dioxide and the alkane corresponding to the carboxylic acid of said solution.

12. The method in accordance with claim 11, wherein said $TiO_2$ powder is partially platinized.

13. The method in accordance with claim 11, wherein said $TiO_2$ powder is selected from the group consisting of anatase doped, anatase undoped, anatase doped platinized, and anatase undoped platinized.

14. The method in accordance with claim 11 wherein said carboxylic acid solution comprises, in aqueous solution, a saturated carboxylic acid selected from the group consisting of acetic, propionic, n-butyric, n-valeric, pivalic and adamante-1-carboxylic, and combinations thereof.

15. The method in accordance with claim 11 wherein said carboxylic acid solution comprises, in aqueous solution, a saturated carboxylic acid and an acetate salt.

16. The method in accordance with claim 15 wherein said carboxylic acid is acetic acid and said salt is sodium acetate.

17. A method for the heterogeneous decarboxylation of a saturated aliphatic carboxylic acid solution on an n-type semiconductor powder, comprising:
    providing at least about 15 mL of aliphatic carboxylic acid solution;
    providing at least about 100 mg of n-type $TiO_2$ powder;

mixing said powder into said solution, to form a mixture;

irradiating said mixture for at least about one hour at a temperature of said mixture of at least about 42° C. until carbon dioxide gas is evolved;

to form as the major reaction products carbon dioxide and the alkane corresponding to said carboxylic acid.

18. The method in accordance with claim 17, wherein said $TiO_2$ powder is partially platinized.

19. A method in accordance with claim 17, wherein said $TiO_2$ powder is selected from the group consisting of anatase doped, anatase undoped, anatase doped platinized, and anatase undoped platinized.

20. The method in accordance with claim 17 wherein said carboxylic acid solution comprises, in aqueous solution, a saturated carboxylic acid selected from the group consisting of acetic, propionic, n-butyric, n-valeric, pivalic and adamante-1-carboxylic, and combinations thereof.

21. The method in accordance with claim 17 wherein said carboxylic acid solution comprises, in aqueous solution, a saturated carboxylic acid and an acetate salt.

22. The method in accordance with claim 21 wherein said carboxylic acid is acetic acid and said salt is sodium acetate.

* * * * *

UNITED STATES PATENT OFFICE
CERTIFICATE OF CORRECTION

Patent No. 4,303,486  Dated December 1, 1981

Inventor(s) Allen J. Bard and Bernhard Kraeutler

It is certified that error appears in the above-identified patent and that said Letters Patent are hereby corrected as shown below:

(Col. 11, line 54), in the "major products" column, the fifth entry from the top, insert -- $CO_2$ -- after "n-butane,".

(Col. 11, line 66), the comma after "cleanly" should be a semicolon.

(Col. 12, line 39), the "of" between "presence" and "absence" should read -- or --.

Signed and Sealed this

Sixteenth Day of March 1982

|SEAL|

Attest:

GERALD J. MOSSINGHOFF

Attesting Officer  Commissioner of Patents and Trademarks